United States Patent [19]

Teague, Jr. et al.

[11] 4,336,622

[45] Jun. 29, 1982

[54] POWER TOOTHBRUSH OR THE LIKE WITH ORBITAL BRUSH ACTION

[76] Inventors: Walter D. Teague, Jr., Tweed Blvd., Nyack, N.Y. 10960; Arthur T. Sempliner, 37-04 Van Nostrand Pl., Douglaston, N.Y. 11363

[21] Appl. No.: 247,514

[22] Filed: Mar. 24, 1981

Related U.S. Application Data

[62] Division of Ser. No. 70,689, Aug. 29, 1979, Pat. No. 4,276,672, which is a division of Ser. No. 848,807, Nov. 7, 1977, Pat. No. 4,175,299.

[51] Int. Cl.$^3$ .............................................. A46B 13/06
[52] U.S. Cl. ..................................... 15/22 R; 128/47; 173/73
[58] Field of Search ........................ 15/22 R; 128/47; 173/73, 168, 169; 51/170 MT; 418/49; 73/258

[56] References Cited

U.S. PATENT DOCUMENTS

| 807,299 | 12/1905 | Marshall | 15/22 R X |
| 839,392 | 12/1906 | Kelly | 73/258 |
| 1,005,024 | 10/1911 | Griner | 128/47 |
| 1,495,010 | 5/1924 | Ford | 73/258 |
| 2,439,262 | 4/1948 | Nalbach et al. | 15/22 R |

Primary Examiner—Edward L. Roberts
Attorney, Agent, or Firm—Mandeville and Schweitzer

[57] ABSTRACT

The disclosure relates to a power toothbrush or the like characterized particularly by the fact that the brush element is driven in an orbital path, as distinguished from a more conventional angularly reciprocating motion. To particular advantage, the power driven brush may be motivated by a water powered nutating action motor mounted in the handle of the unit, although alternative arrangements, including conventional electric motor units, may be used to power the device. In the preferred appliance, an orbital output motion of a nutating drive motor is converted to rotary motion, and this in turn is converted back to an orbital motion in the brush or working element. In other forms of the device, the orbital output of the nutating motor is imparted directly to the working element. The latter arrangement has advantages of greater simplicity, while the former arrangement has advantages of greater compactness.

4 Claims, 15 Drawing Figures

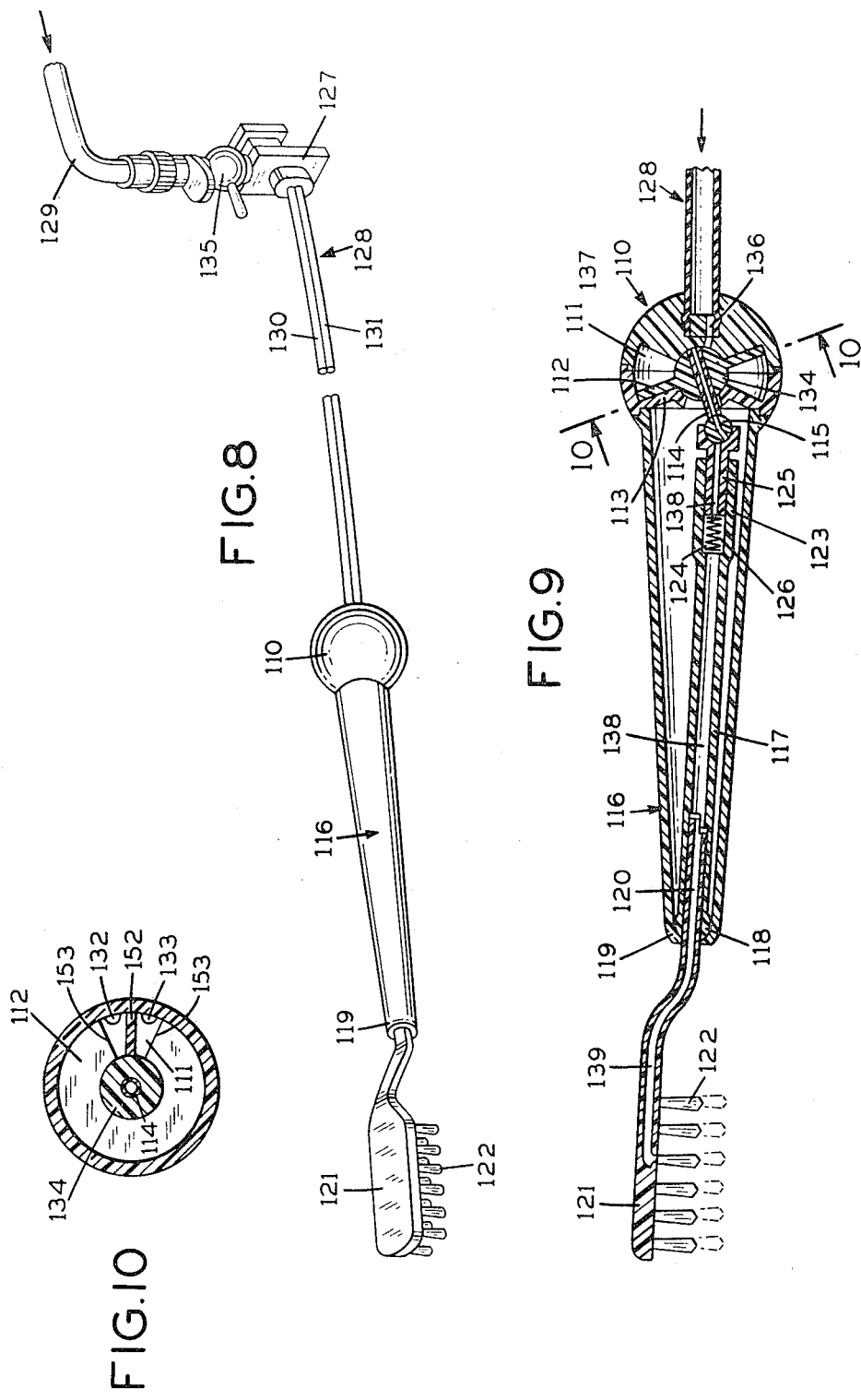

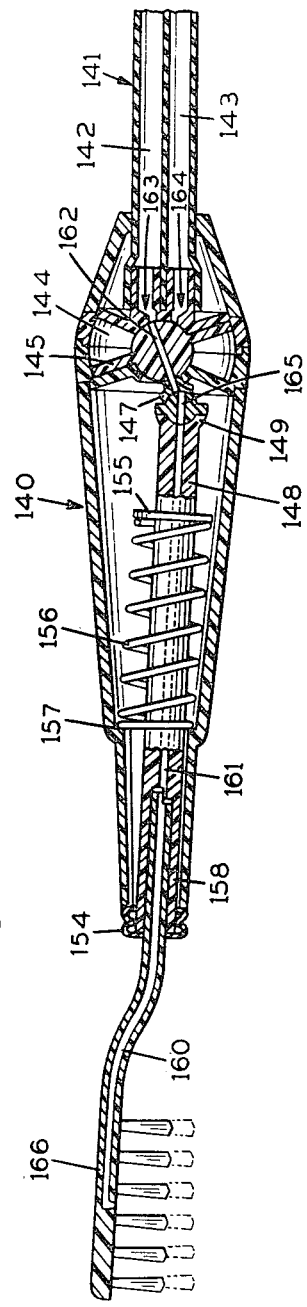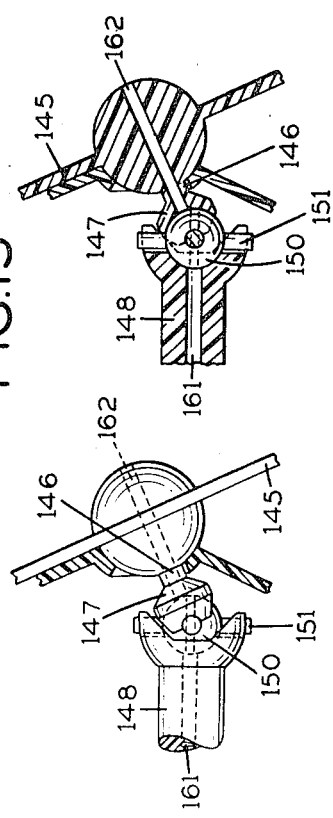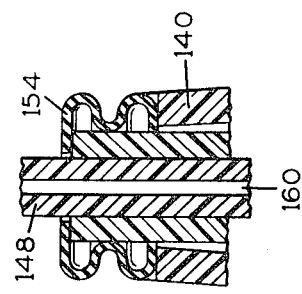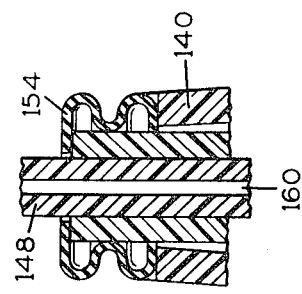

POWER TOOTHBRUSH OR THE LIKE WITH ORBITAL BRUSH ACTION

This is a division of application Ser. No. 70,689, filed 8/29/79, now U.S. Pat. No. 4,276,672, which in turn is a division of application Ser. No. 848,807 filed 11/7/77, now U.S. Pat. No. 4,175,299.

BACKGROUND AND SUMMARY OF THE INVENTION

Power toothbrushes are well known and widely used home appliances. Typically, these devices are electrically driven, utilizing either a rotary electric drive or a form of reciprocating, vibratory drive. The working element (i.e., the brush) typically is driven a reciprocate either linearly or through a limited rotary motion. In either case, the working element executes a back and forth motion over the teeth and gums. In accordance with one aspect of the present invention, a new and improved powered toothbrush appliance is provided in which the working element is arranged to execute an orbital motion, such that the primary working stroke of the brush over the teeth and/or gums is effectively largely unidirectional. During the return motion of the brush, its orbital path tends to retract it away from the teeth and gums, or at least lessen the pressure during the return stroke. This motion provides a brush stroke which approximates the theoretical ideal, in that the primary working stroke can be unidirectional, from the base of the gums, either upward or downward as the case may be, toward the tips of the teeth. The motion is reversable, of course, so that the working stroke may be in an upward direction for the lower teeth and in a downward direction for the upper teeth.

In one of the most advantageous forms of the invention, motive power is provided by a water driven nutating motor having an orbitally moving output element. Pursuant to one aspect of the invention, in order to minimize the overall length of the appliance, from the base of the handle to the tip of the brush, the orbital motion of the nutating motor is converted to a rotary motion through an intermediate drive member, and this drive member in turn imparts the desired orbital motion to the working element or brush.

Where somewhat greater overall length of the appliance is not objectionable, the orbital output of the nutating motor may be imparted directly to the working element. The latter arrangement is characterized by greater mechanical simplicity, but requires somewhat greater length in order to achieve an orbital path of proper dimensions at the tip of the working element.

In accordance with a still further aspect of the invention, a powered toothbrush appliance is provided, in which the working element is caused to execute the desired reversable orbital path, being driven, however, by a conventional rotary electric motor, mounted in the handle of the appliance. This has the advantage of extreme simplicity.

In any of the water-powered versions of the new appliance, provision may be made for controllably diverting at least a portion of the motive fluid—water—into the shank of the brush, to be discharged into the bristle area at the head of the brush. This provides a highly efficient moistening and rinsing action, so that brushing with dentifrice and rinsing may be completed in a single, continuous operation, without interruption for obtaining rinse water from another source.

For a more complete understanding of the above and other features and advantages of the invention, reference should be made to the following detailed description of preferred embodiments of the invention, and to the accompanying drawings.

DESCRIPTION OF THE DRAWINGS

FIG. 8 is a simplified perspective representation of a water driven brush appliance according to the invention, connected to a faucet outlet or the like through an attachment fitting provided for that purpose.

FIg. 9 is a longitudinal cross sectional view through the toothbrush appliance of FIG. 8, illustrating internal details of construction.

FIG. 10 is a cross sectional view as taken generally along line 10—10 of FIG. 9.

FIG. 11 is a longitudinal cross sectional view of a further modified form of the toothbrush appliance of the invention.

FIGS. 12 and 13 are enlarged, fragmentary illustrations of a universal joint arrangement incorporated in the appliance of FIG. 11.

FIG. 14 is an enlarged, fragmentary cross sectional view illustrating the manner of mounting the brush holding element in the appliance of FIG. 11.

DESCRIPTION OF PREFERRED EMBODIMENTS OF THE INVENTION

Figure 1:
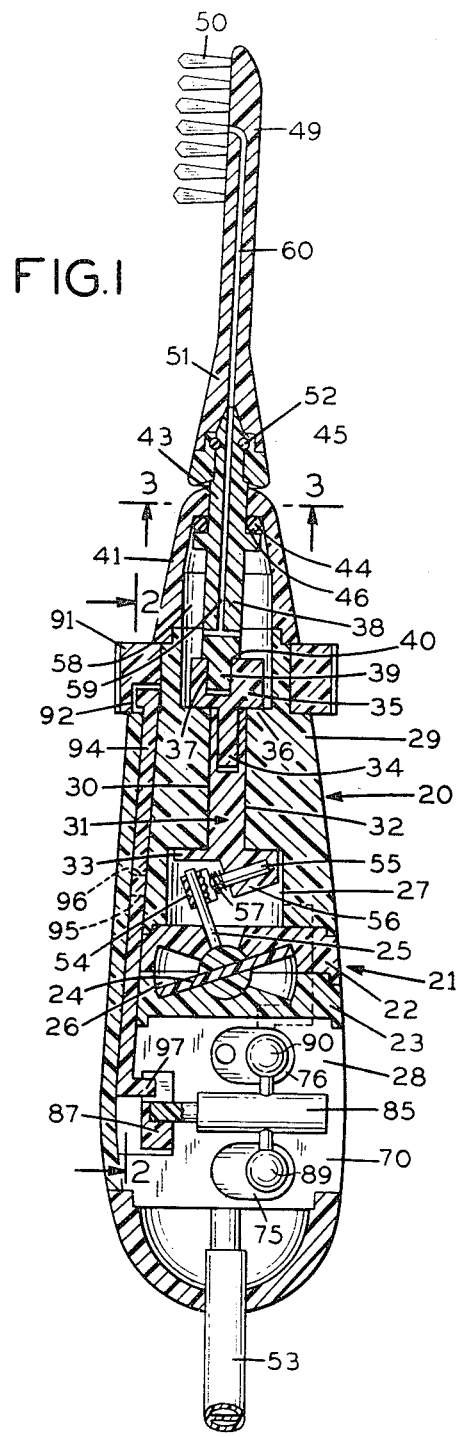
FIG. 1 is a longitudinal cross sectional view of a water driven toothbrush appliance forming a preferred embodiment of the invention.

Referring now to the drawings, and initially to FIGS. 1-6 thereof, the reference numeral 20 designates generally the body or handle portion of a power toothbrush appliance. Desirably, the body portion, as well as most of the internal and working parts of the device are comprised of precision moldings of suitable structural plastic material joined by adhesive or mechanical means, as deemed appropriate to the circumstances. In the device of FIG. 1, a nutating action drive motor 21 is provided, which consists of upper and lower motor casings 22, 23, the exterior surfaces of which may form part of the body 20. Internally, the motor casing 21 mounts a so-called Saturn disc 24, from which extends an output rod 25. The nutating action motor does not, in and of itself, form an invention of the present application, and reference may be made to our copending application Ser. No. 827,625, filed Aug. 25, 1977, and also in our copending application Ser. No. 848,806, filed Nov. 7, 1977, U.S. Pat. No. 4,175,359, further details relating to specifics of the nutating action motor. For the purpose of this disclosure, it is sufficient to note that motive fluid, in this case water, enters the motor chamber 26 on one side of a vertical divider plate (not specifically shown) and flows circumferentially around the chamber, exiting at a discharge port on the opposite side of the dividing plate. In thus traveling around the chamber 26, the motive fluid progressively displaces the Saturn disc, causing it to execute a progressive wobbling motion, without rotation. The output rod 25 is thus caused to execute an orbital motion within the chamber 27. The direction of orbital movement of the upward rod 25 may be reversed by reversing the direction of fluid flow through the motor chamber 26, and this is accomplished in the illustrated device by means of a reversing valve 28 mounted in the lower part of the housing 20, to be described in further detail.

Journaled in an intermediate portion 29 of the appliance body is a rotary transmission element 30. To simplify assembly, the transmission element 30 consists of a lower shaft section 31 which extends through and is rotatably supported by a cylindrical bearing passage 32 in the housing. The shaft section 31 has an enlarged head portion 33, which is received in the chamber 27 and, among other functions, acts as a thrust bearing.

The upper end portion of the shaft section 31 is recessed for the reception of an upper shaft section 34. The upper and lower shaft sections 31, 34 are drivingly connected, either by a splined association therebetween, or by being bonded together during the initial assembly operation. The enlarged head 35 of the upper shaft element seats against a thrust bearing surface 36 to provide rotary support for the upper shaft element.

As reflected in FIG. 1, the upper portion 35 of the upper shaft section 34 is provided with a radially offset, angularly disposed recess 37 for the reception of a wobble shaft 38, the shaft having a cylindrical extension 39 which is received within the recess 37, for relative rotation of the rotary transmission element 30 in relation to the wobble shaft. The shaft 38 has a shoulder 40 arranged for cooperation with the upper end of the rotary shaft head 35 to provide thrust support for the wobble shaft.

Figure 3:
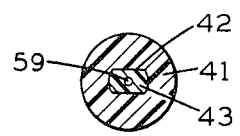
FIGS. 2 and 3 are fragmentary cross sectional views as taken generally on lines 2—2, 3—3 respectively of FIG. 1.

As shown particularly in FIGS. 1 and 3, the upper end of the appliance housing 20 is formed by a cap 41 of generally frusto-conical configuration. The upper end of the cap 41 is provided with a noncircular opening 42 which receives with minimum but slight clearance a similarly configured neck portion 43 of the wobble shaft. Directly under the neck portion 43, the wobble shaft is again of circular cross section and receives an O-ring 44. The O-ring is captured between an internal shoulder 45 on the cap 41 and an upwardly facing shoulder 46 formed on the wobble shaft. The O-ring 44 thus forms a resilient universal pivot mounting for the wobble shaft, permitting an orbital wobble motion of the shaft upon rotation of the rotary shaft element 31.

The upper extremity of the wobble shaft 38 is provided with a recess 47 located just below its upwardly tapered extremity 48 (see FIG. 7). This upper end extremity is adapted to releasably retain a brush head 49 having a bristle section 50 at its outer end. The brush head 49 has an enlarged lower end 51, provided with an internal socket complementary to the upper end extremity of the wobble shaft. Both the socket and the end 48 of the wobble shaft are of noncircular cross section so that the brush head does not rotate with respect to the wobble shaft. An O-ring 52 is received in the socket of the brush head, for releasable engagement with the recess 47 in the wobble shaft, to lock the brush head to the shaft in a firm yet releasable manner.

As reflected in FIG. 1, the appliance body 20 is connected at its lower end to a length of Siamese tubing 53, having individual pressure and exhaust channels therein. The tubing is connected to the reversing valve 28, to be described in further detail, and the reversing valve is connected in turn to the motor chamber 26, on opposite sides of the dividing plate. Depending on the setting of the reversing valve, the saturn disc 24 of the nutating motor will be motivated to move its output rod 25 either clockwise or counterclockwise through an orbital path. The upper portion of the motor output rod 25 is rotatably received within a bearing pad 54 of a plunger 55 slideably received within a lug 56 provided on the shaft head 33. A coil spring 57 constantly urges the plunger 55 toward the operating rod 25 of the nutating disc, at all times maintaining the disc tilted or canted to the maximum extent. For further details of this and other yieldable canting arrangements for the Satura disc, reference may be made to our copending applications Ser. No. 848,806 and Ser. No. 827,625. A significant advantage to be derived from this arrangement is that the disc is at all times maintained properly and fully canted, taking into consideration variations in original manufacturing tolerances, wear from sustained use, and like conditions. Moreover, should for some reason the mechanism become jammed or stalled, the spring 57 can yield against the pressure of the motive fluid within the motor chamber, allowing the motor to stall and bypass fluid without damaging the unit.

When the disc 24 is motivated through its orbital motions, the operating rod 25 serves to rotate the rotary shaft assembly 30 abouts its axis. The wobble shaft 38, being fixed against rotation by the housing cap 41, does not rotate with the upper portion 35 of the rotary shaft. However, because of the offset, angular orientation of the socket 37, the lower end 39 of the wobble shaft is caused to move through an orbital path. This in turn causes the outer end of the brush head 49 to move through an orbital path, as the wobble shaft 38 pivots universally within the O-ring 44.

In accordance with one aspect of the invention, one side of the water system, most advantageously the exhaust side, is connected through internal passages in the appliance housing to the chamber 58 surrounding the lower end of the wobble shaft 38. Passages 59 are provided within the wobble shaft, which connect with a passage 60 in the brush head. The passage 60 discharges into the bristle section 50 of the brush head, as indicated in the drawing.

In conjunction with the above described system of water passages, means are provided for controllably introducing back pressure in the discharge or exhaust side of the Siamese tubing 53. When such back pressure is provided, at least some of the exhaust water being discharged continuously from the nutating motor 21 is forced through the passages 59, 60 and is discharged into the bristle area 50 to provide a desirable rinsing action.

Figure 6:
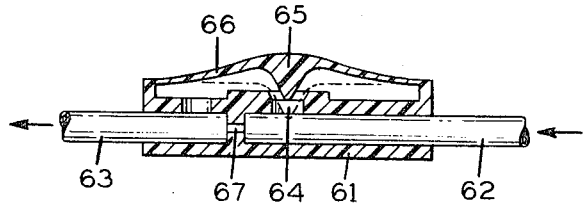
FIG. 6 is a simplified cross sectional view of a manual control valve arrangement, providing a controlled discharge of water through the brush head of the appliance.

An advantageous form of back pressure control arrangement is illustrated in FIG. 6. A valve housing 61 is connected into the exhaust portion 62, 63 of the Siamese tubing. At a position convenient for manual manipulation by the operator. Alternatively, the control may be located on the appliance itself. In either instance, provision is made in the valve body for relatively unrestricted flow of the exhaust water, through a control passage 64 from section 62 of the exhaust tubing to section 63 thereof. The valve passage 64 cooperates with a valve member 65 mounted on or formed integrally with a manually deformable diaphragm 66 positioned for convenient engagement by the operator's thumb or finger. When the diaphragm 66 is depressed, the valve element 65 closes the passage 64 to restrict the flow of exhaust liquid through the outlet tubing. Desirably, the tubing section 62, 63 are joined by a passage 67 of limited cross section, such that when the valve 65 fully closes the passage 64, a minimum flow of exhaust flow is still permitted through the Siamese tubing, with the remainder being discharged through the bristle area 50 for rinsing purposes.

Figure 4:
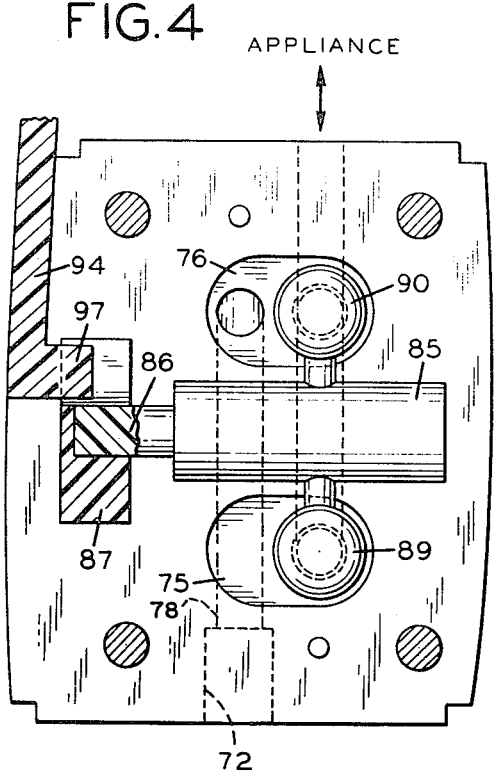
FIG. 4 is vertical cross sectional view illustrating a reversing valve arrangement advantageously incorporated in the appliance of FIG. 1.
Figure 5:
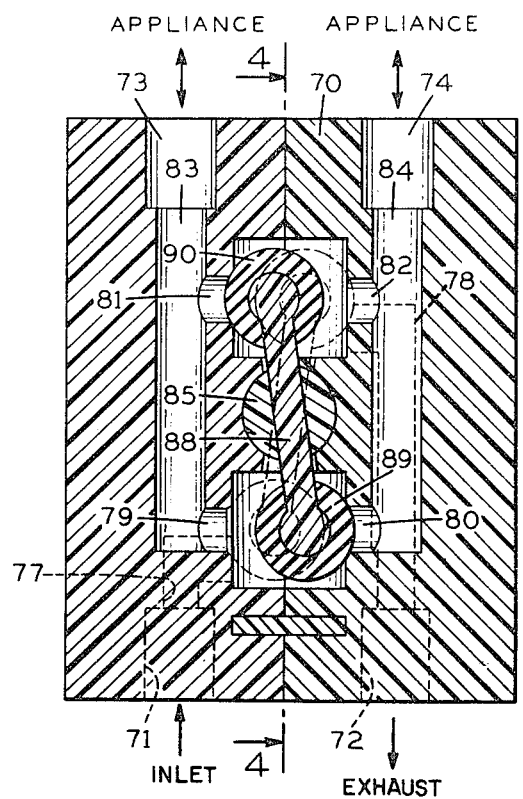
FIG. 5 is a second vertical cross sectional view of the reversing valve of FIG. 4, taken at right angles to the view of FIG. 4.

With reference now particularly to FIGS. 4 and 5, an advantageous form of reversing valve for use in connection with the appliance of FIG. 1 comprises a molded plastic body, preferably contoured so as to form an integral part of the appliance body or handle. The body 70 of the valve includes inlet and exhaust ports 71, 72 respectively at its lower end. At the upper end, there are provided ports 73, 74, which are alternately pressure or exhaust, depending on the setting of the valve. The lower ports 71, 72 are connected to the respective sides of the Siamese tubing 53, while the upper ports 73, 74 are connected to the nutating motor 21, on opposite sides of its dividing plate.

Within the valve body 70 there are formed internal chambers 75, 76 connected by passages 77, 78 to the respective inlet and outlet port 71, 72. Accordingly, the chamber 75 may be considered a pressure chamber, while the chamber 76 may be considered an exhaust chamber. Each of the chambers 75, 76 has opposed outlet ports 79, 80 in the case of the chamber 75, and 81, 82 in the case of the chamber 76. The ports 79, 81, on one side, connect with a common passage 83 leading to the port 73 connected to the nutating motor. Likewise, the chamber ports 80, 82 on the opposite side connect with a common passage 84, leading to the port 74.

Figure 2:
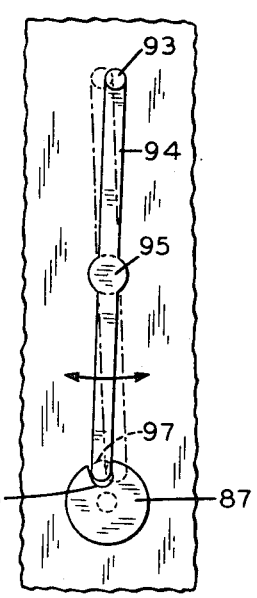

Mounted rotatably within the valve plug 70 is a control shaft 85, an extension 86 of which projects out from the valve plug and mounts an operating wheel 87 (FIG. 2). The inner portion 85 of the operating shaft carries a cross bar 88, opposite ends of which project into the respective pressure and exhaust chambers 75, 76. At its ends, the cross bar 88 is enlarged and rounded for the reception of resilient valve spheres 89, 90. The geometrical arrangement of the cross bar and valve spheres 89, 90 is such that, when the shaft 85 is rotated in one direction to a limit position, the valve spheres will move into closing position with respect to upper and lower ports on opposite sides. Thus, in the positions shown in FIG. 5, the lower sphere 89 closes the port 80 leading into the common passage 84, while opening the pressure chamber 75 to the common passage 83, through the opposite port 79. The upper sphere 90 opens the port 82, connecting the common passage 84 to the exhaust chamber, while closing off the passage 83 thereto. Thus, when the valve member is in the position illustrated in FIG. 5, pressure fluid is supplied to the nutating motor through the valve outlet port 73, while the exhaust fluid from the motor returns through port 74. When the valve element is moved to its other position, pressure fluid is supplied to the motor to the valve port 74, reversing the direction of the motor.

Appropriate means may be provided for rendering the movable valve elements, including the cross bar 88 and shaft 85, self-holding in either operative position. This may be accomplished in various ways, as by mechanical detent means or by slightly unbalancing the valve element. For example, the exhaust chamber ports 81, 82 may be made slightly smaller than the pressure chamber ports 79, 80, so that forces tending to keep the valve closed in any position are somewhat greater than those tending to open it. Similar results can be achieved by providing for asymmetry in the extension of the cross bar element 88, to be slightly longer on the side entering the pressure chamber than on the side entering the exhaust chamber. In many cases, the slight pressure drop in the flow of fluid along the common passages 83 or 84 from the pressure chamber provides a sufficient pressure differential to impart self-holding characteristics to the valve.

For convenience, provision is made for manipulation of the reversing valve 28 by means of a control ring 91 (FIG. 1) which is mounted on the appliance body 20, just below the cap 41, in a position to be easily engaged by the thumb of an operator holding the main body of the appliance. The ring, which is arranged for limited rotation, has an internal recess 92 engaging the upper end 93 of a pivoted control level 94 (FIG. 2). The lever 94 has a cylindrical boss 95 in its center portion, which is received in a corresponding cylindrical recess 96 in the appliance body. The entire lever 94 is contained within a narrow vertical recess in the handle body, which accommodates a limited pivoting movement, typically a total swing of about 3°. At the lower end extremity of the control lever 94, there is a lug 97 which is received in a recess 98 in the control wheel 87 which is fixed to the valve operating shaft. The geometric relationship of the parts is such that, upon relatively small (e.g., 3°) movement of the control lever 94, the control wheel 87 will have a somewhat more magnified motion of, say, 15°, sufficient to switch the reversing valve from one operative position to another. The arrangement provides for reversing of the orbital movement of the brush head 49, by a convenient, side-to-side motion of the thumb of an operator holding the appliance.

Figure 7:
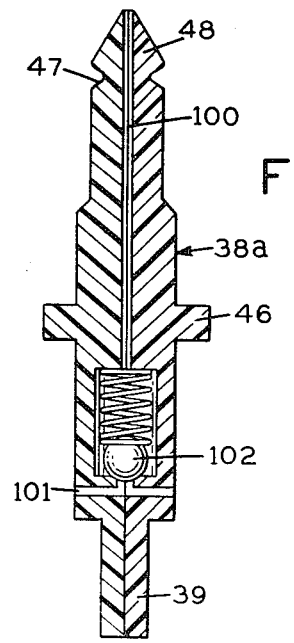
FIG. 7 is a longitudinal cross sectional view of a modified form of brush mounting element arranged for advantageous incorporation in the appliance of FIG. 1.

FIG. 7 illustrates a modified form of wobble shaft which may be used to advantage in the appliance of FIG. 1. In the modified form of shaft, identified generally by the reference numeral 38a, internal water passages 101, for the discharge of water into the brush head, are controllably blocked by a spring loaded check valve 102. This provides a more positive control over the discharge of water through the brush head, since a higher level of back pressure in the discharge line must exist before the flow of water commences through the check valve 102.

It is also possible, of course, to divert inlet pressure up to the brush head through a controllable on-off valve, but it is usually more convenient to divert water from the exhaust side of the nutating motor for this purpose.

Referring now to FIGS. 8–10, there is illustrated a modified form of the invention, in which the orbital output motion of a nutating motor is imparted directly to a brush head-supporting wobble shaft in a toothbrush appliance. Thus, in FIG. 9, the reference numeral 110 designates generally the lower housing of the appliance, which forms a casing for a nutating drive motor. The housing 110 defines a chamber 111 supporting and containing a Saturn disc 112 of the nutating motor. The general principles of operation of the motor itself are similar to those of the motor described in connection with FIGS. 1–8, with certain exceptions to be noted. The upper wall 113 of the motor housing has an opening through which extends an operating rod 114 which, in this case, is of tubular cross section. The operating rod 114 carries a spherical element 115 at its outer end extremity.

An upper housing portion 116, which forms a hand grip, extends from the lower housing 110 and houses an elongated, tubular wobble shaft 117. The wobble shaft 117 has a bearing element 118 at its outer end, which cooperates with a correspondingly shaped bearing socket 119 formed in the end of the upper housing 116. The arrangement of the bearing 118 and bearing socket 119 is such as to accommodate limited universal pivoting movement of the wobble shaft 117, while preventing rotation thereof.

The outer end of the wobble shaft 117 is recessed to non-rotatably receive the shank 120 of a removable brush head 121 provided with bristles 122 of a conventional character.

Pursuant to the invention, the inner end 123 of the wobble shaft is provided with a cylindrical recess 124 for the slideable reception of a bearing plunger 125. The outer end of the bearing plunger has a spherical socket for the reception of the end of the motor operating rod 114, and the plunger is at all times yieldably urged toward the operating rod by a small spring 126 positioned in the upper end of the recess 124.

In the assembled appliance, the bearing plunger 125 constantly urges the operating rod 114, and thus the Saturn disc 112 of the nutating motor, to a position of maximum tilt or cant within the chamber 111. This assures optimum positioning of the disc 112, while at the same time accommodating minor variations in dimensions of the parts through manufacturing tolerances, wear, etc. As in the case of the previously described embodiment, the yieldable canting of the Saturn disc provides for automatic pressure relief, in the event the mechanism becomes jammed or stalled, inasmuch as the water can tilt the disc slightly toward a neutral position, against the action of the spring 126, to permit water flow through the motor housing without further progressive displacement of the disc.

In the arrangement of FIGS. 8–10, a suitable removable attachment 127 may be provided for connection of a Siamese tubing 128 to a conventional faucet outlet 129. The attachment 127 fastens to the end of the faucet and, when the water is turned on, diverts pressure water through one of the passages 130 of the Siamese tubing. Return water is directed through the other passage 131 and is ultimately discharged through the bottom of the attachment 127.

As reflected in FIG. 10, the separate passages of the Siamese tubing are appropriately connected such that one of the passages terminates at an inlet opening 132 in the motor chamber 111, while the outer passage terminates in an exhaust port 133. In a well known manner, fluid entering the inlet port 132 travels circumferentially around the motor chamber, progressively tilting the disc 112, which is supported for limited universal movement by a spherical bearing 134. The resulting orbital output movement of the operating rod 114 is transmitted directly to the wobble shaft 117 and brush head 121.

In order to reverse the orbital motion of the brush head 121, it is necessary to reverse the flow of flow through the motor chamber 111. In the embodiment illustrated in FIGS. 8–10, this may be accomplished by a reversing valve 135 forming part of the faucet attachment 127. In the embodiment of FIGS. 8–10, provisions are made for periodic discharge of rinse water through the brush head 121 during a portion of each cycle of the nutating motor. This is achieved by providing a small duct 136 leading from each of the passages 130, 131 of the Siamese tubing 128 and terminating at the spherical bearing seat 137 for a Saturn disc 112. The location of the ducts 136 is such that, during portions of the orbital cycle of the lower end of the tubular operating rod 114, the interior of the operating rod is aligned with the ducts 136. When that alignment occurs with the duct which is under pressure, water momentarily flows through the operating rod and into a passage 138 of the bearing plunger 125. The water then flows through an internal passage 138 in the wobble shaft and through a like passage 139 in the brush head, to be discharged in the bristle area. With the described arrangement, a pulsating flow of rinse water is provided through the brush head during operation of the device. If desired, of course, the inlet source to the passages 136 may be selectively valved, such that the pulsating rinse water supply may be turned on or off as desired by the user.

The embodiment of FIGS. 11–14 is similar in basic function to that of FIGS. 8–10, in that the orbital output of a nutating motor is transmitted directly to a brush head-supporting wobble shaft. A main handle-forming casing 140 is connected to a Siamese tubing 141 leading from an appropriate source of water under pressure and a reversing valve. Individual passages 142, 143 of the tubing lead, by passages not illustrated, to the interior of the motor chamber 144, on opposite sides of its divider plate. A Saturn disc 145, constituting the movable element of the nutating motor, has an output element 146, on which is mounted a socket 147 forming a portion of a universal drive joint. A tubular wobble shaft 148 is provided at its lower end with a similar socket portion 149 forming another part of the universal joint drive. The two socket portions 147, 149 mutually engage a spherical bearing 150 provided with pairs of radially extending rods 151. The arrangement is such that the operating element 146 of the nutuating motor is non-rotatably connected to the wobble shaft 148. By this means, the wobble shaft may be maintained against rotation by the Saturn disc 145 (or vice versa). Thus, the Saturn disc 145 normally is prevented from rotating by means of the divider plate (see item 152, FIG. 10), which is straddled by edges of the plate forming the Saturn disc. Reference may be made to edges 153, FIG. 10, which illustrates a corresponding construction in the motor in the embodiment of FIGS. 8–10. By thus non-rotatably joining the output element 146 in the wobble shaft 148, the desired orbital movement of the wobble shaft may be achieved while the shaft is retained against rotation. In addition, it may be desirable to provide means, such as a flexible boot 154, by means of which the upper end of the wobble shaft 148 is secured to the upper end of the appliance housing 140. The flexible boot 154 permits the intended orbital wobbling movement of the shaft 148 while preventing rotation thereof.

Within the housing 140, the wobble shaft 148 is provided with a flange 155. A spring 156 is seated on the flange 155 and also against an internal shoulder 157 in the housing such that the spring urges the entire wobble shaft 148 down into the housing 140, toward the output element 146 of the nutating motor. The spring 156 thus serves to normally maintain the Saturn disc 145 fully canted, while providing for pressure relief in the event of stall or overload. The flexible boot 154 provides for limited axial displacement of the wobble shaft 148 to accommodate such relief, as will be understood.

As in the case of the embodiment of FIGS. 8–10, the wobble shaft 148 internally receives the shank 158 of a replaceable brush head 159. Also as in the case of the embodiment of FIGS. 8–10, internal passages 160, 161 are provided in the brush head and wobble shaft for the supply of rinse water for discharge in the bristle area of the brush. A passage 162 through the spherical bearing of the Saturn disc, which periodically communicates with passages 163, 164 in the motor housing, and with a passage 165 in the universal bearing sphere 150, provides for periodic pulsating discharge of water through the brush. The pulsating discharge may, of course, be valved if desired. Likewise, the discharge of water through the brush head, when valved on, may be made continuous, if desired, by appropriate recessing of the relatively movable passage-forming parts, so that constant, rather than periodic, communication is provided during movement of the Saturn disc.

As will be understood, a two-axis universal joint mechanism, such as utilized in the device of FIGS. 11–14 does not have "constant speed" characteristics under rotation, when the drive elements are disposed at an angle. Similar characteristics are evident in the mechanism of the invention, even though the parts do not rotate about their axis but merely move through an orbital path. By properly orienting the universal joint mechanism in relation to the bristles of the brush head, it is possible to derive relatively increased power during the working stroke of the bristles and relatively increased speed during non-working motions.

Figure 15:
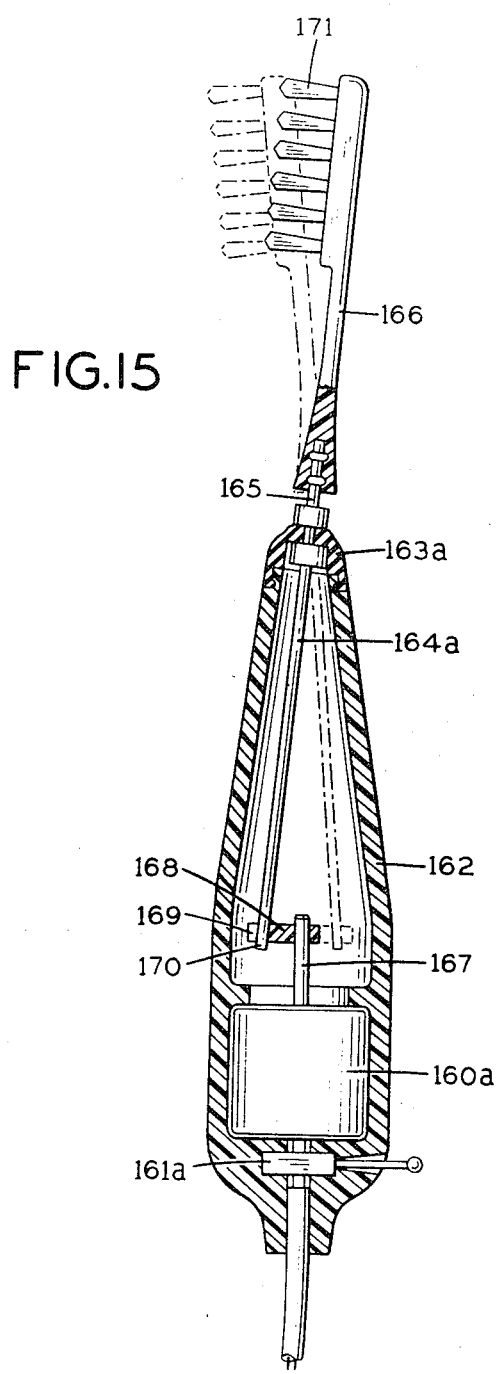
FIG. 15 is a longitudinal cross sectional view of a further modified form of a new appliance, in which the brush element is driven in an orbital path by an electric motor drive.

In the modification illustrated in FIG. 15, an orbital motion toothbrush appliance is provided which is driven by a relatively conventional, rotary electric motor 160a controlled for reversable rotation by the manually operated reversing switch 161 in the base of the appliance housing 162. At the upper end of the housing 162 there is provided a housing cap 163a which, in the illustrated example, is constructed of a resilient material. The cap 163a supports for limited universal pivoting movement a wobble shaft 164a. The outer end 165 of the wobble shaft is arranged to mount a removable brush head 166. As in the case of the previously described embodiments, the wobble shaft 164a is non-rotatable relative to the housing 162, and the brush head 166 is non-rotatable relative to the wobble shaft.

Pursuant to the invention, the output shaft 167 of the electric motor carries a displacement arm 168 provided with a notch 169 in its outer end. The lower end 170 of the wobble shaft is received in this notch. Accordingly, when the motor shaft 167 is rotated, the lower end of the wobble shaft is driven through an orbital path as a function of the effective radius and rotation of the displacement arm 168. This orbital motion of the wobble shaft is translated directly to the brush head 166 to achieve the desired orbital motion of the bristles 171. Reversing of the orbital motion of the brush head is of course accomplished by reversal of motor rotation through the switdh 161a.

In any of its various forms, the power driven toothbrush of the invention enables a highly advantageous orbital brush action to be achieved in a simple and effective way. The orbital action, with a capability of reversal of direction, approaches a theoretical ideal motion for cleaning of the teeth.

In all forms of the invention, the desired orbital output motion of a brush head is achieved by means of an orbitally driven wobble shaft, which is non-rotatably mounted in the appliance housing, for universal pivoting movement at a point adjacent the outer end of the housing. The brush head extends outward from this point and, in the area of the bristles, describes an orbital path whose diameter desirably is of around 5.5 mm. In all cases, however, in the region of the universal pivot point, the orbital path of the brush head approaches zero. Thus, in the area where the brush appliance enters the mouth, its motion is very small, and the size of the housing can be very small. At the same time, the orbital motion at the brush head proper is entirely adequate for the purposes intended.

The embodiments of FIGS. 1–14 all make advantageous use of a novel form of water-driven nutating motor, which can utilize faucet water as a power source, with simple and convenient provisions for diverting some of that water through the brush head for rinsing purposes. In the embodiments of FIGS. 8–14, the orbital output of the nutating motor is imparted directly to the brush head-supporting wobble shaft, such that the orbital motion of the nutating motor is transmitted directly to the brush head. In the modification of FIGS. 1–7, provisions are made for initially converting the orbital motion of the nutating motor to pure rotary motion, and then for re-converting that rotary motion back to an orbital motion of a brush head-supporting wobble shaft. The last mentioned embodiment, while introducing an additional mechanical stage, has certain practical advantages with respect to reducing the overall length of th appliance. In this respect, in a nutating motor of appropriate size and power for the purpose intended, the output rod will have a diameter of orbital movement of a given size. To convert that orbital movement to a desired (e.g., 5.5 mm diameter) orbital movement of a brush head of convenient and standardized length (e.g. 70 mm) the length of the wobble shaft necessarily is relatively long. By first converting the orbital motion of the motor to purely rotary motion, the wobble shaft may be driven by a displacement arm or member, whose diameter of orbital motion may be precisely predetermined to achieve the desired output orbit at the brush head with a wobble shaft of shortest practicable length.

In the modification of FIGS. 1–7, the arrangement of the mechanism to provide orbital-to-rotary-to-orbital motion enables the working mechanism to be sufficiently compacted axially that, in a manual appliance of appropriate size to be hand held, a reversing valve may be conveniently built into the appliance. This may be controlled by simple side-to-side movement of the thumb, while the device is in use, such that the working stroke of the brush may be converted from downward to upward with great facility and speed.

It should be understood, of course, that the specific forms of the invention herein illustrated and described are intended to be representative only, as certain changes may be made therein without departing from the clear teachings of the disclosure. Moreover, although the features of the invention are illustrated in the embodiment of a power driven toothbrush, many of the mechanisms and features incorporated therein are applicable in other environments. Accordingly, reference should be made to the following appended claims in determining the full scope of the invention.

We claim:

1. A powered toothbrush appliance or the like, which comprises
   (a) a housing,
   (b) a non-rotatable, orbitally movable wobble shaft mounted for universal pivoting movement in said housing,
   (c) said wobble shaft including a first end supporting a working element and a second driven end,
   (d) orbital output drive means in said housing comprising a fluid-powered, nutating action motor having an orbitally moving output element,
   (e) means directly connecting the orbitally moving output element of the nutating action motor to the driven end of the wobble shaft.

2. A powered toothbrush according to claim 1, further characterized by
   (a) yieldable means on said wobble shaft operative to urge said output element into an angular position.

3. A powered toothbrush according to claim 2, further characterized by
   (a) said wobble shaft having a recess at its driven end,
   (b) said yieldable means including a bearing plunger slideably received in said recess, and spring means acting between said bearing plunger and the wobble shaft,
   (c) said bearing plunger being arranged to mechanically couple the driven end of the wobble shaft to the output element and,
   (d) said spring means urging said plunger toward said output element.

4. A powered toothbrush according to claim 2, further characterized by
   (a) flexible means connecting said wobble shaft to said housing and accommodating limited axial movement of said wobble shaft, and
   (b) said yieldable means comprising a spring means acting between said housing and said wobble shaft to urge said shaft toward said output element.

* * * * *